(12) United States Patent
Georgakis et al.

(10) Patent No.: US 6,379,147 B1
(45) Date of Patent: Apr. 30, 2002

(54) DENTAL IMPRESSION TRAY ASSEMBLY WITH REMOVABLE LINER

(75) Inventors: Evangelos G. Georgakis, Alta Loma; Brian W. Lotte, Redondo Beach, both of CA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/603,066

(22) Filed: Jun. 26, 2000

(51) Int. Cl.[7] .................................................. A61C 9/00
(52) U.S. Cl. ............................................ 433/37; 433/47
(58) Field of Search ........................... 433/37, 47, 48, 433/71

(56) References Cited

U.S. PATENT DOCUMENTS

| | | | |
|---|---|---|---|
| 2,598,927 A | * 6/1952 | May | ............... 433/47 |
| 2,963,786 A | 12/1960 | Browning | |
| 3,250,004 A | 5/1966 | Jones | |
| 4,063,552 A | 12/1977 | Going et al. | |
| 4,445,854 A | 5/1984 | Bekey et al. | |
| 4,776,792 A | * 10/1988 | Wagner et al. | ............... 433/71 |
| 4,867,680 A | 9/1989 | Hare et al. | |
| 5,011,407 A | * 4/1991 | Pelerin | ............... 433/48 |
| 5,026,278 A | 6/1991 | Oxman et al. | |
| 5,040,976 A | 8/1991 | Ubel, III et al. | |
| 5,108,286 A | * 4/1992 | Freedman et al. | ............... 433/37 |
| 5,316,473 A | 5/1994 | Hare | |
| 5,395,239 A | * 3/1995 | Komatsu et al. | ............... 433/71 X |
| 5,403,185 A | * 4/1995 | Presswood | ............... 433/74 |
| 5,487,662 A | 1/1996 | Kipke et al. | |
| 5,551,872 A | * 9/1996 | Mena | ............... 433/37 |
| 5,718,577 A | 2/1998 | Oxman et al. | |
| 5,772,432 A | 6/1998 | Jordan et al. | |
| 5,890,895 A | 4/1999 | Tucker | |
| 6,017,217 A | 1/2000 | Wittrock | |

FOREIGN PATENT DOCUMENTS

DE         210868        6/1909

* cited by examiner

Primary Examiner—Nicholas D. Lucchesi
(74) Attorney, Agent, or Firm—James D. Christoff

(57) ABSTRACT

A dental impression tray assembly includes an impression tray as well as a liner. The liner is adapted to cover holes in the impression tray in order to prevent leakage of impression material through the holes during a dental procedure. Preferably, the liner is removably connected to the tray so that the practitioner has the option of using the tray with or without the liner.

29 Claims, 4 Drawing Sheets

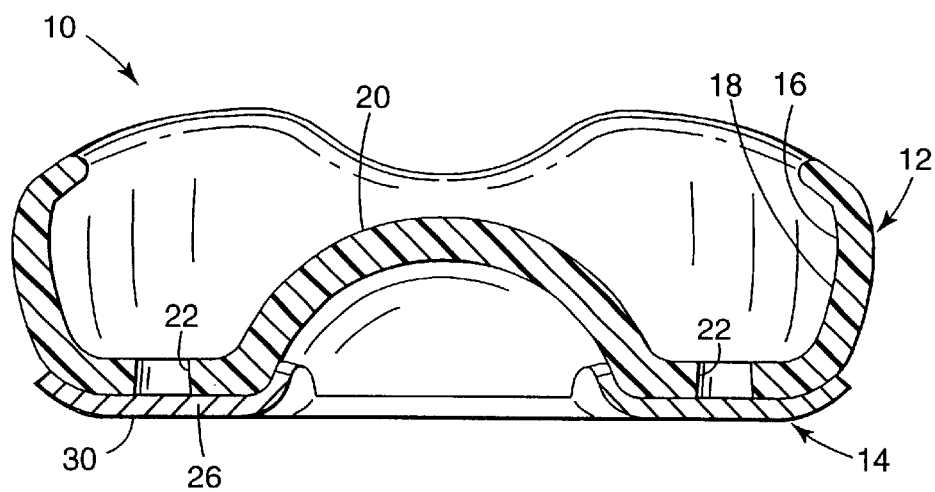
*Fig. 3*
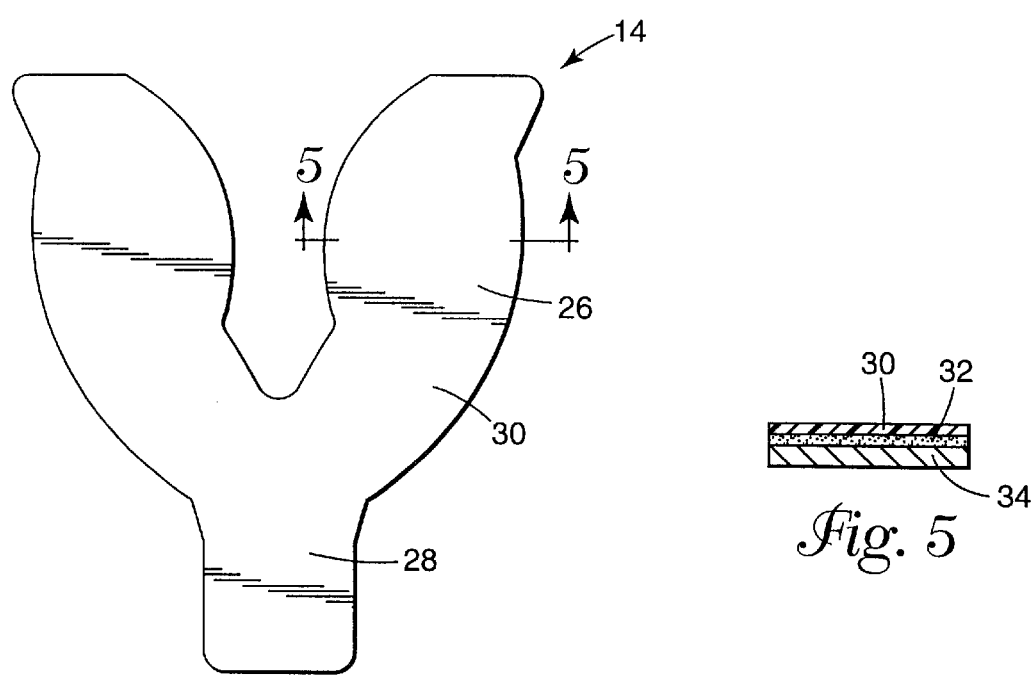
*Fig. 4*
*Fig. 5*

DENTAL IMPRESSION TRAY ASSEMBLY WITH REMOVABLE LINER

BACKGROUND OF THE INVENTION

1. Field of the Invention

This invention relates to a dental impression tray assembly and a method of preparing a dental impression tray for use.

2. Description of the Related Art

Dental impression trays are often used by dentists, orthodontists, prosthodontists and others engaged in various fields of dentistry for obtaining a model or replica of selected areas of a patient's oral cavity. For example, a dentist or prosthodontist may desire to have a model of an area of a patient's oral cavity where one or more teeth are missing or damaged, so that suitable replacement teeth may be made in the lab using the model as a guide. In practice, the replacement teeth may be fitted by trial and error on the model and adjusted in size and shape as needed until a satisfactory size and shape are attained.

As another example, orthodontists often use models of a patient's teeth to study malformations of the teeth and jaws and plan a course of treatment. In some instances, the orthodontist may use models to trial fit one or more orthodontic appliances that will be used in the oral cavity to move teeth to desired positions. In other instances, models may be used to pre-position a set of orthodontic brackets and associated archwires that are later affixed to the patient's actual dental arches by a technique known as indirect bonding. Models are also used by orthodontists as well as other dental practitioners to serve as a permanent record of a patient's teeth before and after treatment, and sometimes at selected intervals during the treatment program.

The use of dental models provides significant advantages for both the dental practitioner and the patient. Models enable the dental practitioner to adjust the shape and size of replacement teeth and tooth restorations and to adjust the position of orthodontic appliances and the like in the practitioner's laboratory or in an outside laboratory as desired and during a time that is most convenient for the dentist or lab personnel. Moreover, such initial size, shape and position adjustments can be carried out without requiring the patient to wait in the dental chair. Once a satisfactory fitting of the replacement teeth, restoration or orthodontic appliances is obtained on the model, the practitioner can readily install the same in place in the patient's oral cavity with few or no additional adjustments in many instances.

To obtain a dental model, an impression of desired areas of the patient's oral cavity is first obtained. To prepare an impression, a quantity of curable dental impression material is placed in an impression tray, and the tray is then positioned in the patient's oral cavity such that the impression material fills and surrounds the selected area of interest of the oral cavity. Once the impression material has cured, the impression material along with the tray is removed from the oral cavity.

To make a dental model from the impression, a second curable material is poured or otherwise placed in the cured impression material. Once the second material has cured, the impression material is removed from the resulting model. When made properly, the model provides an accurate physical replica of selected areas of the patient's tooth structure as well as adjacent portions of the patient's gingiva if desired.

A variety of dental impression trays are available to hold dental impression material as impressions are made. Some dental impression trays have an overall, generally "U"-shaped configuration in plan view that matches the overall, generally "U"-shaped configuration of the patient's upper or lower dental arch. Other impression trays have an overall, generally "J"-shaped configuration in plan view for making an impression of one quadrant of the patient's oral cavity (i.e., the right or left half of either the patient's upper dental arch or lower dental arch). Still other impression trays have a generally straight configuration in plan view and are particularly useful in instances where an impression of areas representing less than a complete quadrant is needed.

Typically, a certain area of the dental impression tray serves as a receptacle for receiving dental impression material. In many dental impression trays, the receptacle comprises a channel having a generally "U"-shaped configuration in views transverse to the longitudinal axis of the channel (i.e., in reference planes perpendicular to the occlusal or "bite" plane of the patient). Other dental impression trays simply have a flat or generally flat surface for receiving the impression material. Some dental impression trays such as the tray described in U.S. Pat. No. 4,445,854 have upwardly-facing receptacles and downwardly-facing receptacles so that impressions of the upper and lower dental arch can be simultaneously obtained.

Dental impression trays are commercially available in a variety of materials. Some impression trays are made of metal such as stainless steel or aluminum. Other impression trays are made of a rigid plastic material such as polyethylene or polypropylene, or made of polystyrene foam (such as "STYROFOAM" brand polystyrene foam from Dow Chemical Company). Examples of impression trays made of a thermoplastic material that is malleable at elevated temperatures are described in U.S. Pat. Nos. 5,040,976 and 5,026,278.

A variety of dental impression materials are also commercially available. Elastomeric impression materials are generally preferred because the flexibility of the elastomeric material when cured enables the material to be readily removed from the oral cavity even when undercut areas, recesses and the like are present in the tooth structure. However, non-elastomeric impression material (such as plaster of Paris) has also been used in the past to a limited extent.

Elastomeric dental impression materials are often considered to fall in one of five major classes: reversible hydrocolloids, irreversible hydrocolloids, polysulfides, silicones and polyethers, of which the last four are thermosetting. An example of an irreversible hydrocolloid impression material is "UNIJEL-II" brand alginate impression material from 3M Unitek Corporation. An example of a silicone dental impression material is "EXPRESS" brand impression material from 3M Company.

Often, a means is provided to securely connect the impression material to the impression tray so that the impression material does not inadvertently detach from the receptacle of the impression tray. For example, when removing an impression tray bearing a quantity of elastomeric impression material from the patient's oral cavity, a significant force must sometimes be exerted on the tray in order to cause the cured impression material to flexibly deform as needed to disconnect from undercut areas or recesses of certain tooth structure. In such instances, the impression material should remain securely connected to the impression tray so that both the material and the tray are removed as a single unit from the oral cavity.

Some impression trays have holes or perforations placed along the receptacle to provide a mechanical means for coupling the impression material to the tray. In other instances, an adhesive is used to chemically bind the impression material to the receptacle of the tray. An example of a tray adhesive used in connection with alginate impression material is "HOLD" brand tray adhesive from Teledyne Getz. Tray adhesives are particularly useful for alginate and other hydrocolloid impression material that have little, if any, adhesive qualities.

Tray adhesives are conventionally used by the dental practitioner by applying the adhesive to the receptacle of the tray that receives the impression material immediately before the impression is to be taken. The impression material is then placed in the receptacle and the impression is made in the manner described above.

U.S. Pat. No. 5,772,432 describes an improved dental impression tray with a receptacle for receiving the dental impression material. The receptacle is coated with an adhesive to enhance the bond between the impression material and the tray. The adhesive is applied to the tray body at least 16 hours before the impression material is placed in the receptacle. Advance coating of the adhesive onto the tray body provides a higher bond strength between the impression material and the tray than would otherwise be observed. Additionally, precoating of the impression tray by the manufacturer reduces the risk that the patient will experience a burning sensation or irritation due to one or more solvents that might otherwise volatilize from the tray adhesive during use in the oral cavity, or that might be caused by direct contact of the tray adhesive with the patient's gingiva.

However, some impression materials are somewhat fluid and may leak through holes in the tray, causing a nuisance to the practitioner and possibly also to the patient. The problem of leakage is particularly noticeable when alginate impression materials are mixed by the practitioner to a somewhat thin, runny consistency. Unfortunately, the use of a tray adhesive does not significantly reduce the likelihood of dripping of impression materials through the holes, especially in instances when the impression material is relatively thin and fluid.

As can be appreciated, there is a need in the art for an impression tray that provides enhanced retention of impression material in the tray receptacle and yet avoids the problem of leakage of impression material from the receptacle, even when relatively fluid impression materials are used. Preferably, such an impression tray would be relatively inexpensive and yet adaptable to a variety of different uses according to the preferences of the practitioner for the situation at hand.

SUMMARY OF THE INVENTION

The present invention is directed toward a dental impression tray assembly that has a removable liner. The liner is adapted to extend across at least some of the holes in the tray in order to substantially prevent leakage of impression material through the holes. Preferably, the liner is removably connected to the impression tray so that the practitioner can use the tray without the liner if desired.

In more detail, the present invention is one aspect is directed toward a dental impression tray assembly. The assembly includes a dental impression tray having wall portions defining a receptacle for receiving a quantity of dental impression material. At least some of the wall portions include a number of holes. The assembly also includes a liner that is removably connected to the impression tray. The liner extends across at least some of the holes.

In another aspect, the present invention is directed toward a dental kit. The kit includes a dental impression tray having wall portions defining a receptacle for receiving a quantity of dental impression material. At least some of the wall portions include a number of holes. The kit also includes an impression tray liner for connection to the impression tray. The liner extends across at least some of the holes when connected to the impression tray.

The present invention is also directed to a dental impression tray liner. The liner comprises a barrier sheet and an adhesive extending over at least part of the barrier sheet. The barrier sheet includes a portion having a generally "U"-shaped configuration for connection to the dental impression tray.

Another aspect of the present invention is directed toward a method of preparing a dental impression tray for use. The method includes the act of selecting an impression tray suitable for taking an impression of oral structure of interest. The method also includes the act of connecting a liner to the tray in order to cover at least one hole in the tray.

These and other aspects of the invention are described in more detail in the text that follows and are illustrated in the accompanying drawings.

BRIEF DESCRIPTION OF THE DRAWINGS

FIG. 3 is a vertical sectional view of the assembly shown in FIGS. 1 and 2;

FIG. 4 is a plan view of the liner of the assembly shown in FIGS. 1–3 before the liner is connected to the impression tray;

FIG. 5 is a side cross-sectional view (not to scale) of the liner illustrated in FIG. 4, taken along lines 5—5 of FIG. 4;

DETAILED DESCRIPTION OF THE DRAWINGS

Figure 1:
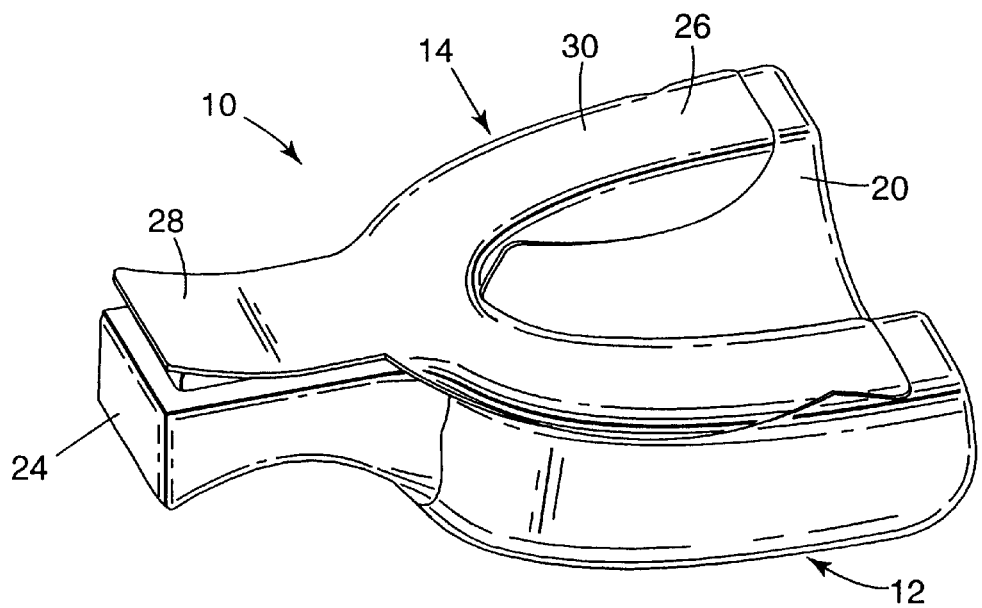
FIG. 1 is a perspective view showing a bottom side of a dental impression tray assembly according to the present invention, wherein the assembly includes a dental impression tray as well as a liner.
Figure 2:
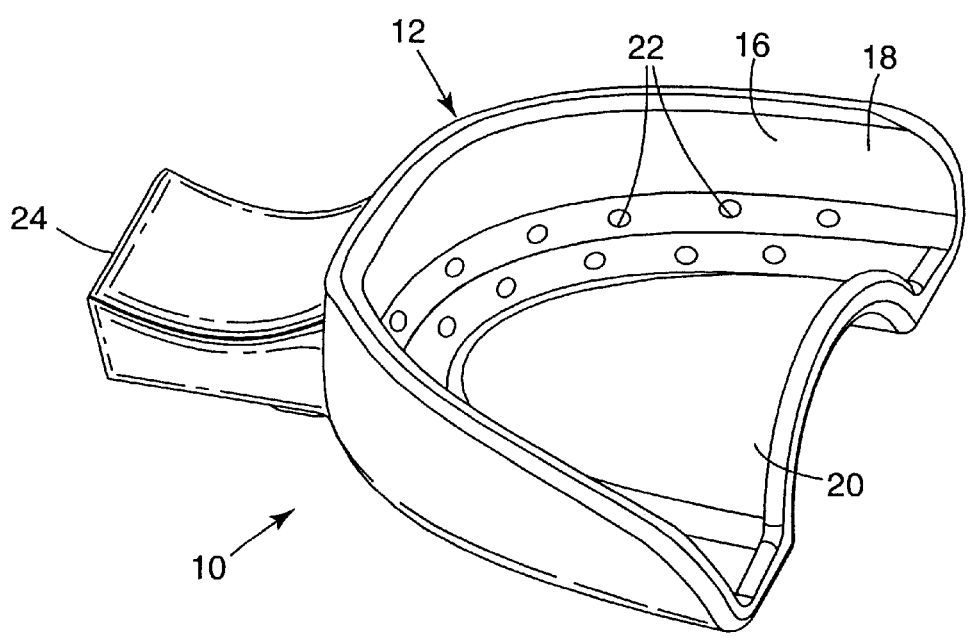
FIG. 2 is a perspective view of the dental impression tray assembly shown in FIG. 1, illustrating a top side of the impression tray.

A dental impression tray assembly according to one embodiment of the invention is broadly designated by the numeral 10 in FIGS. 1–3. In brief, the assembly 10 includes a dental impression tray 12 as well as a liner 14. In this embodiment, the liner 14 is initially connected to the tray 12 by the manufacturer, and is preferably removable from the tray 12 by the end user if desired.

The impression tray 12 includes wall portions 16 that define a receptacle 18 for receiving a quantity of dental impression material. In this example, the tray 12 including the receptacle 18 has an overall, generally "U"-shaped configuration in plan view in order to take an impression of the entire upper dental arch of the patient. Consequently, the size and curvature of the "U"-shaped configuration of the receptacle 18 may vary as needed to fit the dental arch of a particular patient, and the manufacturer may opt to provide a number of trays 12 in various sizes and configurations.

Moreover, the impression tray may have a shape other than that which is shown in the drawings. For example, the impression tray may have an overall, generally "J"-shaped configuration in plan view for taking an impression of one quadrant or an overall, but somewhat smaller generally "U"-shaped configuration for taking a partial arch impression. As another alternative, the impression tray may have a generally straight configuration in plan view for use in instances where an impression of an area representing less than a complete quadrant is needed.

The wall portions 16 and the receptacle 18 also have a generally "U"-shaped configuration in vertical reference planes, as can be appreciated by reference to FIGS. 2 and 3. The wall portions 16 along the inner side of the receptacle 18 are connected to a central support 20 that provides a space for the patient's tongue when an impression is taken. The support 20 is also useful for holding the impression material against the patient's palate.

The impression tray 12 that is shown in FIGS. 1–3 is adapted for taking an impression of the patient's upper dental arch. However, the invention is also useful for trays adapted for taking impressions of the patient's lower dental arch. The central support 20 is eliminated for trays that are intended to take an impression of a lower dental arch.

At least some of the wall portions 16 that define the receptacle 18 are provided with a number of holes 22. In the illustrated embodiment, the holes 22 are arranged along the upper wall portions 16 that extend along the top of the receptacle 18, although other locations are also possible. Although not shown in the drawings, the support 20 may also be provided with one or more holes if desired.

The holes 22 provide a mechanical coupling between the impression tray 12 and the impression material once the impression material is cured. Optionally, the tray 12 may also be provided with other types of mechanical means for enhancing retention of the impression material in the tray 12, such as a series of grooves or ridges that are spaced along the wall portions 16. As another option, the tray 12 could be provided with a tray adhesive that is used to chemically bind the impression material to the wall portions 16. Moreover, the tray adhesive may be precoated by the manufacturer as described in U.S. Pat. No. 5,772,432 which is incorporated by reference herein.

The tray 12 also includes a rear handle portion 24 that projects outwardly from a middle region of the "U"-shaped configuration of the tray 12. The handle portion 24 facilitates grasping the tray 12 and positioning the tray 12 in the patient's oral cavity as desired. Optionally, an upper side of the handle portion 24 is provided with a circular cavity.

Preferably, the tray 12 is integrally made of a synthetic resinous material such as polystyrene foam. Optionally, the tray 12 may be similar or identical to the polystyrene foam impression trays sold by 3M Unitek Corporation, Catalog Nos. 436-630 to 436-639. Alternatively, the tray 12 may be made of other materials such as aluminum, stainless steel, polypropylene or polyethylene.

The liner 14 includes a first section 26 having a generally "U"-shaped configuration that somewhat matches the "U"-shaped configuration of the receptacle 18. Additionally, the liner 14 includes a handle section 28 that extends outwardly from a middle region, and preferably from the center, of the first liner section 26. Preferably, the first section 26 has a shape that covers most of the holes 22 when the liner 14 is connected to the tray 12, and more preferably has a shape that covers all of the holes 22 when the liner 14 is connected to the tray 12.

FIGS. 4 and 5 are illustrations of the liner 14 before the liner 14 is connected to the tray 12. The liner 14 includes a barrier sheet 30 as well as a layer of adhesive 32 that extends across the barrier sheet 30. Preferably, the barrier sheet 30 is impervious to the selected impression material and does not chemically react with the selected impression material. An example of a suitable material for the barrier sheet 30 is a synthetic resinous material such as polyetheylene although other materials are also possible.

The adhesive 32 is preferably a pressure sensitive adhesive, such as an acrylate pressure sensitive adhesive. Optionally, the liner 14 initially includes a release sheet 34 that initially extends across the layer of adhesive 32 for protection of the adhesive 32 until such time as the liner 14 is applied to the tray 12. The release sheet 34 is particularly useful in instances where the liner 14 and the tray 12 are not assembled to each other when shipped to the end user since the release sheet 34 in that instance can protect the layer of adhesive 32 from contamination. An example of a suitable release sheet 34 is polyethylene coated kraft paper.

An example of a suitable liner 14 is known as plastic medical tape on liner, Catalog No. 1523, from 3M Company, which includes a barrier sheet, a layer of adhesive and a release sheet or liner. Other materials may also be used. The release sheet 34 may be omitted if desired, particularly if the assembly 10 is sold with the liner 14 pre-assembled to the tray 12.

As another option, the liner 14 may include a flavoring aid that provides a pleasing flavor when the assembly 10 is placed in the oral cavity. The flavor aid may be used to counteract an undesirable flavor of the impression material, the tray adhesive or other substance. Particularly preferred flavors include spearmint, peppermint and cherry.

Preferably, the layer of adhesive 32 does not extend along the handle section 28 of the liner 14. As such, the handle section 28 does not adhere to the handle portion 24 of the tray 12 so that the liner 14 is easy to grasp when desired. Sometimes, the practitioner may prefer to use the tray 12 without the liner 14, and in those instances the practitioner may pull on the handle section 28 in order to detach the liner 14 from the tray 12.

As can be appreciated, the liner 14 substantially prevents the leakage of dental impression material from the receptacle 18 and through the holes 22. As a result, the impression material does not drip on the user's hands before the assembly 10 is placed in the patient's oral cavity, avoiding what might otherwise be a substantial nuisance. Additionally, the impression material does not drip through the holes 22 and onto the patient's teeth, gingiva or tongue during the time that the impression is taken.

Once the impression material has hardened and the impression has been taken, the assembly 10 is removed from the patient's oral cavity. However, in some instances, a significant amount of force may be needed to detach the impression material from the patient's oral structures. This force is often relatively large because the hardened impression material may be difficult to remove from undercut regions, such as the spaces between the patient's teeth that are next to the gingiva, even though the hardened impression material may have a somewhat rubbery consistency. Additionally, the impression material is often closely fitted to the oral structures and a suction force is sometimes encountered when an attempt is made to detach the impression material from the oral structures.

The assembly 10, however, provides a significant advantage when the practitioner is detaching the impression material from the patient's oral structures. In particular, the liner 14 strengthens and provides reinforcement for the tray 12, such that the tray 12 is less likely to fracture when an attempt is made to detach the impression material from the oral structures. This advantage is particularly beneficial when the impression tray 12 is made of polystyrene or other relatively weak plastic materials. Even if the tray 12 does fracture or begins to fracture, the liner 14 helps to retain the tray 12 in assembled relation so that the assembly 10 can be removed from the oral cavity along with the impression material as a single unit.

Optionally, each of the holes 22 has a draft in order to provide an undercut region. In particular, the diameter of the holes 22 increases as the liner 14 is approached. The undercut regions, if present, provide for additional retention of the dental impression material in the receptacle 18.

The wall portions 16 include a first side that faces the receptacle 18 and the oral structure of interest when the tray 10 is in use. The wall portions 16 also include a second side that is opposite the first side and faces away from the oral structure of interest.

Figure 6:
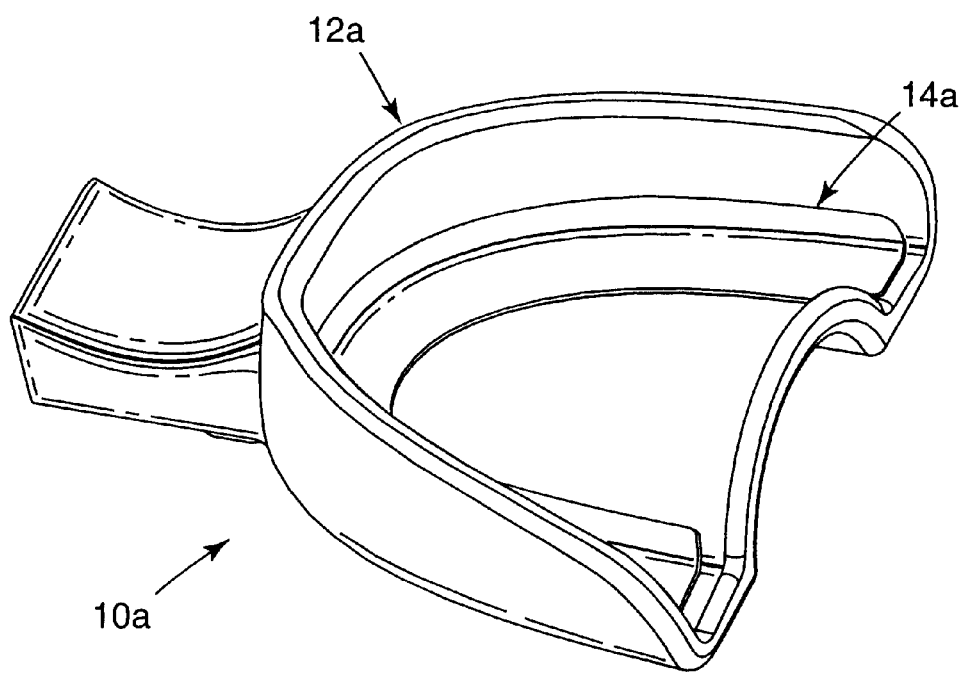
FIG. 6 is a perspective view showing a top side of a dental impression tray assembly according to another embodiment of the invention.

In the embodiment shown in FIGS. 1–3, the liner 14 is connected to the second side of the wall portions 16. However, the liner 14 may also be removably connected to the first side. An example of such construction is shown in FIG. 6, where an assembly 10a includes a tray 12a and a liner 14a.

The assembly 10a is identical to the assembly 10, except as noted. The liner 14a preferably covers all of the holes (not shown) in the tray 12a. However, the liner 14a lacks a handle section such as the handle section 28 of the liner 14.

Figure 7:
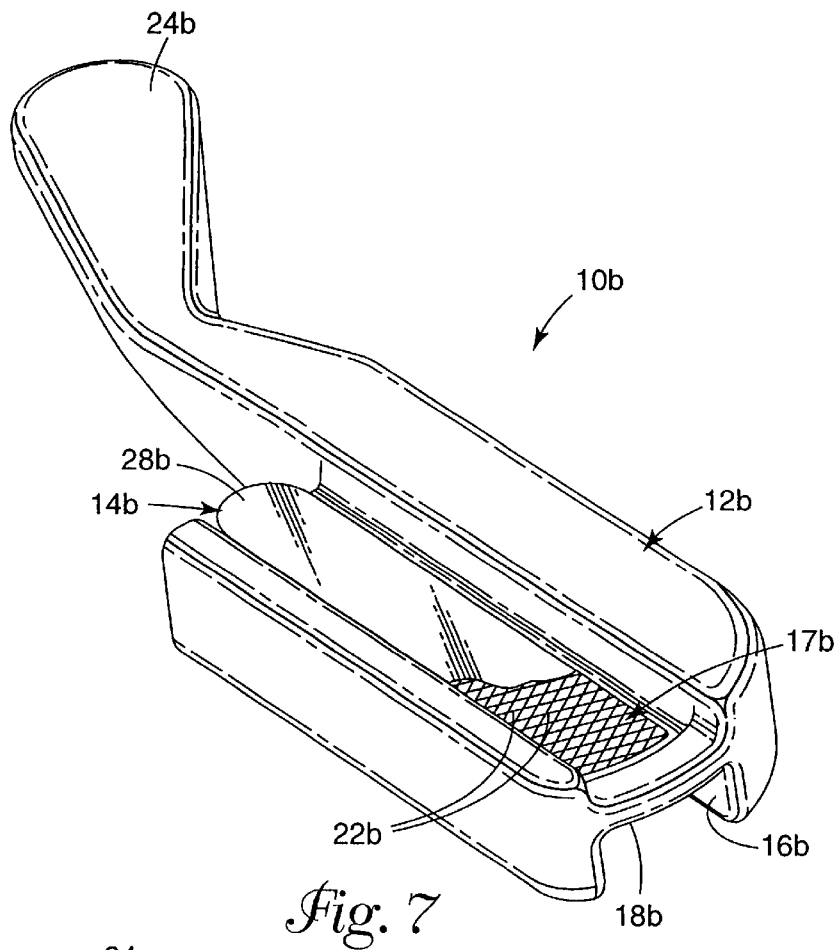
FIG. 7 is a perspective view showing a bottom side of a dental impression tray assembly that is constructed according to still another embodiment of the invention.

A dental impression tray assembly 10b according to another embodiment of the invention is illustrated in FIG. 7. The assembly 10b includes a dental impression tray 12b that, in this instance, has an elongated, substantially straight configuration. The impression tray assembly 10b is particularly useful for taking impressions of only a portion of a patient's dental arch.

The impression tray 12b includes wall portions 16b that define a receptacle 18b. In the example, a bottom wall portion or septum 17b is made of a mesh material, such as a mesh made of interwoven fibers arranged in a diagonal pattern. An example of a suitable mesh material is polyethylene coated with a silicone-based material. Foils, gauzes, and woven fabrics may also be used.

The septum 17b includes a number of openings or holes 22b, at least some of which are covered by a liner 14b. Preferably, all of the holes 22b are covered by the liner 14b. The liner 14b is removably connected to the septum 17b, and optionally has a handle section 28b that extends past the septum 17b to facilitate grasping of the liner 14b when desired.

The impression tray 12b also has a rear handle portion 24b. The handle portion 24b as well as the wall portions 16b (except for the septum 17b) are preferably integrally molded and made of a synthetic resinous material. In FIG. 7, a portion of the liner 14b has been removed to show the underlying septum 17b.

Figure 8:
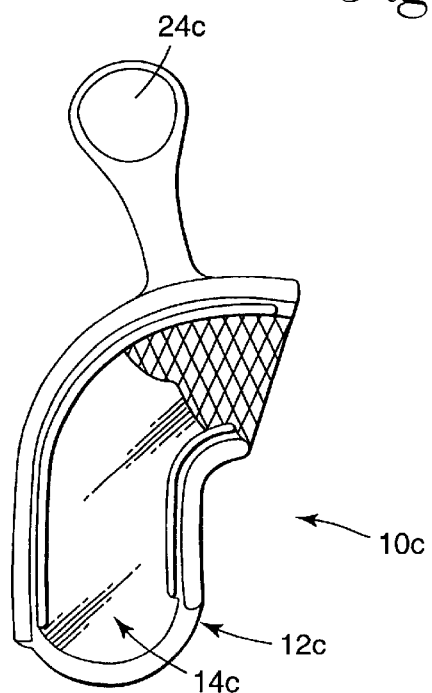
FIG. 8 is a bottom view of a dental impression tray assembly according to yet another embodiment of the invention.

A dental impression tray assembly 10c according to another embodiment of the invention is illustrated in FIG. 8. The assembly 10c includes a dental impression tray 12c and a liner 14c. The tray 12c and the liner 14c both have a somewhat "J"-shaped configuration in plan view in order to take an impression of a dental quadrant.

The impression tray 12c also includes a handle portion 24c that, in this instance, is oriented somewhat differently than the handle portion 24b described above. However, in other aspects, the assembly 10c is essentially the same as the assembly 10b.

Optionally, the tray and liner of the assemblies 10, 10a, 10b and 10c may be provided as part of a dental kit. In that instance, the liner may be initially separate from the tray if desired. As a further option, a number of identical liners may be initially connected together as part of a die-cut web, or may be connected together in a stacked array (similar to a note pad) so that the user can merely detach a single liner from the remaining liners when desired. When connected together in a stacked array, the release sheet (such as sheet 34) between the adjacent liners may be omitted if desired.

Figure 9:
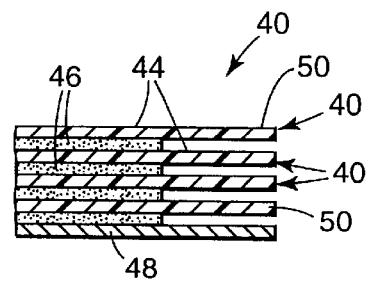
FIG. 9 is a side cross-sectional view (not to scale) of another embodiment of the invention, where a number of liners are releasably connected together in a stacked array.

FIG. 9 is a schematic, side cross-sectional view of an example of a portion of a stacked array of liners. The array 40 in this example includes four liners 42, each of which includes a barrier sheet 44 and a layer of adhesive 46. Additionally, a release sheet 48 is detachably connected to the adhesive layer 46 of the bottom-most liner 42.

Each of the liners 42 of the array 40 includes a handle section 50 (such as the rear handle section 28 described above). The handle section 50 is devoid of any adjacent adhesive 46, and as such is relatively easy to grasp on both sides. When use of a liner 42 is desired, the practitioner may grasp the handle section 50 of the uppermost liner 42 in order to pull the barrier sheet 44 and adhesive 46 away from the next adjacent, underlying liner 42.

The dental kit may also include other items useful in a dental procedure. For example, the dental kit may include a quantity of dental impression material, such as the impression materials described above. Optionally, the kit may also include a tray adhesive and/or a mailer for returning the completed impression to a dental laboratory or other facility remote from the practitioner's office.

A number of other variations of the invention are also possible. Accordingly, the present invention should not be deemed limited to the specific examples that are described in detail above, but instead only by a fair scope of the claims that follow along with their equivalents.

What is claimed is:

1. A dental impression tray assembly comprising:
    a dental impression tray having wall portions defining a receptacle for receiving a quantity of dental impression material, wherein at least some of the wall portions include a number of holes and an outer side facing away from the receptacle;
    a liner removably connected to the outer side of the wall portions and extending across at least some of the holes; and
    an adhesive for removably connecting the liner to the impression tray.

2. A dental impression tray assembly according to claim 1 wherein the holes include undercut regions.

3. A dental impression tray assembly according to claim 1 wherein the adhesive is non-removably connected to the liner.

4. A dental impression tray assembly according to claim 1 wherein the adhesive is a pressure sensitive adhesive.

5. A dental impression tray assembly according to claim 4 wherein the adhesive is an acrylate pressure sensitive adhesive.

6. A dental impression tray assembly according to claim 1 wherein the tray includes a handle portion remote from the receptacle, and wherein the liner includes a section extending across the handle portion.

7. A dental impression tray assembly according to claim 6 wherein the adhesive does not extend between all of the liner section and the handle portion in order to facilitate gripping of the liner when desired.

8. A dental impression tray assembly according to claim 1 wherein the impression tray is made of a synthetic resinous material.

9. A dental impression tray assembly according to claim 8 wherein the impression tray is made of a polystyrene material.

10. A dental impression tray assembly according to claim 1 wherein the dental impression tray is made of a metallic material.

11. A dental impression tray assembly according to claim 1 wherein the impression tray is adapted to take an impression of the upper dental arch.

12. A dental impression tray assembly according to claim 1 wherein the impression tray is adapted to take an impression of the lower dental arch.

13. A dental impression tray assembly according to claim 1 wherein the liner extends across all of the holes when the liner is connected to the impression tray.

14. A dental impression tray assembly according to claim 1 wherein the tray includes a handle portion remote from the receptacle, wherein the liner includes a section extending across the handle portion, and wherein the liner section is not connected to the handle portion in order to facilitate gripping of the liner when desired.

15. A dental impression tray assembly according to claim 1 wherein the dental impression tray has a generally "U"-shaped portion.

16. A dental impression tray assembly according to claim 1 wherein the dental impression tray has an overall, generally "J"-shaped configuration.

17. A dental impression tray assembly according to claim 1 wherein the dental impression tray is elongated and has a substantially straight configuration.

18. A dental tray assembly according to claim 1 and including a quantity of dental impression material.

19. A dental impression tray liner comprising a barrier sheet and an adhesive extending over at least part of the barrier sheet, wherein the barrier sheet has a section having a generally "U"-shaped configuration for connection to a dental impression tray, wherein the barrier sheet includes a handle section that protrudes outwardly from the middle of the "U"-shaped section, the tray liner also including a release sheet initially extending across at least a portion of the adhesive and being removable from the adhesive when desired, and wherein the handle section substantially lacks the adhesive.

20. A dental impression tray liner according to claim 19 wherein the adhesive comprises a layer of a pressure sensitive adhesive.

21. A dental impression tray liner according to claim 20 wherein the adhesive is an acrylate pressure sensitive adhesive.

22. A method of preparing a dental impression tray for use comprising the acts of:
   selecting an impression tray suitable for taking an impression of oral structure of interest;
   removing a release sheet from a dental impression tray liner;
   connecting the dental impression tray liner to an outer side of the tray in order to cover at least one hole in the tray;
   placing a quantity of impression material in a receptacle of the impression tray; and subsequently
   placing the impression tray along with the impression material in the patient's oral cavity.

23. A method of preparing a dental impression tray for use according to claim 22 wherein the act of placing a quantity of dental impression material in a receptacle of the tray includes the act of placing a portion of the dental impression material in undercut regions of at least one hole.

24. A method of preparing a dental impression tray for use according to claim 22 wherein the act of connecting a liner to the tray includes the act of releasably connecting the liner to the tray.

25. An assembly comprising:
   a first dental impression tray liner comprising a barrier sheet and an adhesive extending over at least part of the barrier sheet, wherein the barrier sheet has a section having a generally "U"-shaped configuration for connection to a dental impression tray; and
   a second dental impression tray liner comprising a barrier sheet and an adhesive extending over at least part of the barrier sheet of the second dental impression tray liner, wherein the barrier sheet has a section having a generally "U"-shaped configuration for connection to a dental impression tray, and wherein the second dental impression tray liner is detachably connected to the first dental impression tray liner.

26. The assembly of claim 25 and including a third dental impression tray liner comprising a barrier sheet and an adhesive extending over at least part of the barrier sheet of the third dental impression tray liner.

27. An assembly according to claim 25 wherein the first dental impression tray liner and the second dental impression tray liner have substantially the same configuration.

28. An assembly according to claim 25 wherein the adhesive of each dental impression tray liner comprises a layer of pressure sensitive adhesive.

29. A dental impression tray assembly comprising:
   a dental impression tray having wall portions defining a receptacle for receiving a quantity of dental impression material, wherein at least some of the wall portions include a number of holes; and
   a liner removably connected to the impression tray and extending across at least some of the holes, wherein the liner includes a flavoring agent.

* * * * *